United States Patent [19]
Liu et al.

[11] Patent Number: 5,284,489
[45] Date of Patent: Feb. 8, 1994

[54] FILAMENT FABRICATED FROM A BLEND OF IONOMER RESIN AND NONIONIC THERMOPLASTIC RESIN

[75] Inventors: Cheng-Kung Liu, Norwalk; John C. Brewer, Bristol, both of Conn.

[73] Assignee: United States Surgical Corporation, Norwalk, Conn.

[21] Appl. No.: 932,377

[22] Filed: Aug. 19, 1992

[51] Int. Cl.⁵ .............................................. A61L 17/00
[52] U.S. Cl. ............................... 606/228; 606/230; 606/231; 606/151; 526/351; 525/196; 525/240; 525/221
[58] Field of Search ................ 623/11, 13; 606/228, 606/230, 231, 151; 526/351; 525/240, 196, 221

[56] References Cited

U.S. PATENT DOCUMENTS

| | | |
|---|---|---|
| 2,226,529 | 12/1940 | Austin . |
| 3,054,406 | 9/1962 | Usher . |
| 3,124,136 | 3/1964 | Usher . |
| 3,264,272 | 8/1966 | Rees . |
| 3,322,734 | 5/1967 | Rees . |
| 3,404,134 | 10/1968 | Rees . |
| 3,454,011 | 7/1969 | Wagner . |
| 3,454,676 | 7/1969 | Busse . |
| 3,630,205 | 12/1971 | Listner . |
| 4,172,820 | 10/1979 | Lundberg et al. . |
| 4,193,137 | 3/1980 | Heck . |
| 4,224,946 | 9/1980 | Kaplan . |
| 4,226,751 | 10/1980 | Lundberg et al. . |
| 4,259,284 | 3/1981 | Lundberg et al. . |
| 4,279,344 | 7/1981 | Holloway, Jr. ............... 206/484 |
| 4,343,859 | 8/1982 | Lundberg et al. . |
| 4,343,931 | 8/1982 | Barrows . |
| 4,347,847 | 9/1982 | Usher . |
| 4,452,245 | 6/1984 | Usher . |
| 4,520,821 | 6/1985 | Schmidt et al. . |
| 4,520,822 | 6/1985 | Menezes et al. . |
| 4,557,264 | 12/1985 | Hinsch . |
| 4,578,451 | 3/1986 | Weaver et al. . |
| 4,612,337 | 9/1986 | Fox, Jr. et al. ............... 606/231 |
| 4,620,542 | 11/1986 | Menezes et al. . |
| 4,621,638 | 11/1986 | Silvestrini . |
| 4,633,873 | 1/1987 | Dumican et al. . |
| 4,652,264 | 3/1987 | Dumican . |
| 4,655,221 | 4/1987 | Devereux . |
| 4,690,981 | 9/1987 | Statz ............................. 525/221 |
| 4,838,884 | 6/1989 | Dumican et al. . |
| 4,911,165 | 3/1990 | Lennard et al. . |
| 4,968,752 | 11/1990 | Kawamoto et al. ........... 525/221 |
| 5,002,551 | 3/1991 | Linsky et al. . |
| 5,200,468 | 4/1993 | Pickton . |

FOREIGN PATENT DOCUMENTS 0334046 9/1989 European Pat. Off. .

Primary Examiner—Randall L. Green
Assistant Examiner—Paul Prebilic

[57] ABSTRACT

A filament is fabricated from a biologically acceptable blend of an ionomer resin such as an ionically cross-linked ethylene-methacrylic acid copolymer and a nonionic thermoplastic resin, e.g., a polyolefin such as an isotactic polypropylene.

33 Claims, 4 Drawing Sheets

FILAMENT FABRICATED FROM A BLEND OF IONOMER RESIN AND NONIONIC THERMOPLASTIC RESIN

BACKGROUND OF THE INVENTION

This invention relates to a filament fabricated from a blend of ionomer resin and nonionic thermoplastic resin and to a melt extrusion (spinning) process for fabricating the filament. Among other applications, the filament is useful as a suture and as a surgical mesh.

Nonabsorbable sutures manufactured from various nonionic thermoplastic resins such as polyolefins, polyesters, polyamides, poly(esteramides), copolyether amides, polyether-polyester block copolymers, polyurethane block copolymers, and the like, are known. For further details regarding such sutures, reference may be made to U.S. Pat. Nos. 3,630,205 and 4,911,165 (sutures obtained by the melt extrusion of isotactic polypropylene), U.S. Pat. Nos. 4,520,822 and 4,620,542 (sutures made from ethylene-propylene copolymers), U.S. Pat. No. 4,557,264 (sutures made from blends of polypropylene and linear low density polyethylene), U.S. Pat. No. 4,621,638 (sutures made from polymers capable of forming hard elastic filaments under high stress spinning conditions, e.g., from polyolefins such as isotactic polybutylene, isotactic polypropylene, polyethylene and mixtures of isotactic and non-isotactic polyolefins), U.S. Pat. Nos. 3,297,033, 3,636,945 and 3,839,297 (absorbable sutures fabricated from glycolide-lactide copolyesters), U.S. Pat. No. 4,224,946 (sutures made from polyether-polyester block copolymers), U.S. Pat. No. 2,226,529 (sutures made from polyamides), U.S. Pat. No. 4,343,931 (sutures made from poly(esteramides)), U.S. Pat. No. 4,578,451 (sutures made from polyetheramides) and U.S. Pat. No. 3,454,011 (sutures made from Spandex polyurethane block copolymers).

Knitted and woven fabrics constructed from a variety of synthetic fibers and the use of the fabrics in surgical repair are known from, among others, U.S. Pat. Nos. 3,054,406; 3,124,136; 4,193,137; 4,347,847; 4,452,245; 4,520,821; 4,633,873; 4,652,264; 4,655,221; 4,838,884; and 5,002,551; EPA 334,046; and Wantz, "Atlas of Hernia Surgery", Raven Press, 1991.

Ionomer resins are known, inter alia, from U.S. Pat. Nos. 3,264,272, 3,322,734 and 3,404,134.

Blends of ionomer resins and elastomers such as ethylene/propylene copolymer, butadiene/styrene copolymer, etc., are known from U.S. Pat. No. 3,454,676.

Fibers manufactured from ionomer resins employing a wet or dry spinning process are known from U.S. Pat. Nos. 4,172,820, 4,226,751, 4,259,284 and 4,343,859. The fibers have use in clothing, carpeting and similar applications.

SUMMARY OF THE INVENTION

In accordance with the present invention a filament is provided which is fabricated from a blend of ionomer resin and nonionic thermoplastic resin.

The filament is advantageously fabricated by a process which includes the steps of melt extruding a blend comprising ionomer resin and nonionic thermoplastic resin to provide a filament, cooling the filament, stretching the cooled filament and annealing the stretched filament.

The filament of this invention with or without further processing can be used as a suture which exhibits several improved properties compared to those of a known suture of equivalent construction fabricated entirely from nonionic thermoplastic resin. Thus, the suture herein possesses far fewer voids, if any, than the known suture, a property which results in fewer breaks.

In addition, the suture of this invention exhibits reduced strain energy compared with that of a suture made entirely of nonionic thermoplastic polymer, strain energy being defined as the integration of the measured stress-strain curve for a monofilament measured in kilograms-mm and is equivalent to the work expended in elongating the monofilament by a specified percentage of its original length. The strain energy of a monofilament suture is related to the amount of effort required to straighten the suture upon removal of the suture from its package such that the lower the strain energy the lesser the effort required to straighten the suture prior to use.

Yet another advantage of the suture herein lies in the ability of the ionomer resin component to bond with bioactive substances such as cationic biocidal agents thus providing an effective and convenient device for the long term release of such substances at or near the wound site.

The filament of this invention can also be formed into yarn, fabrics, etc., for a variety of uses including medical/surgical applications, clothing, carpeting, etc. Thus, a surgical mesh fabricated from a yarn made with the filament of this invention can be used as a prosthesis in hernia repair.

DESCRIPTION OF THE PREFERRED EMBODIMENTS

Figure 1:
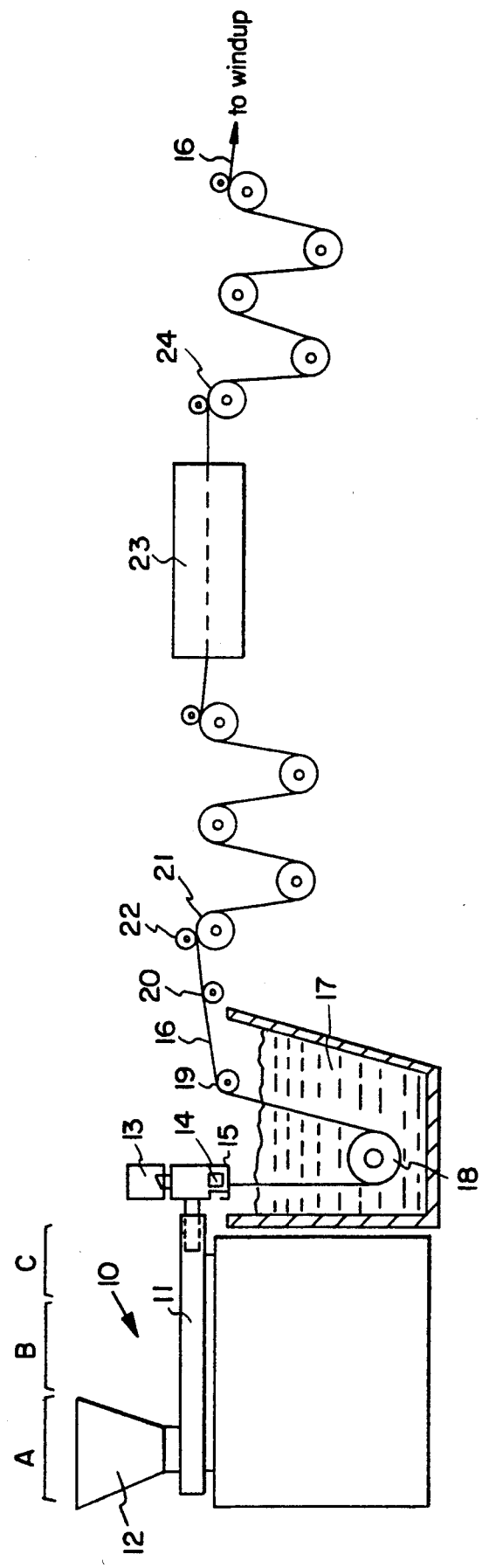
FIG. 1 is a schematic representation of apparatus which is suitable for carrying out the extruding and stretching steps of a preferred melt extrusion process for obtaining the filament of this invention.

The ionomer resins which are utilized in the polymer blends from which the filament of this invention is made are ionically crosslinked thermoplastic resins generally prepared by neutralizing a copolymer containing pendent acid groups, e.g., carboxylic acid groups, sulfonic acid groups and/or phosphonic acid groups, with an ionizable metal compound, e.g., a compound of the monovalent, divalent and/or trivalent metals of Groups I, II, IV-A and VIIIB of the Periodic Table of Elements. See, "Encyclopedia of Polymer Science and Engineering", 2nd Edition, Vol. 8, pp. 393–423 (John Wiley & Sons, 1987), the contents of which are incorporated by reference herein. When the filament is intended for medical use, e.g., as a suture or surgical mesh, the ionomer resin, the nonionic thermoplastic resin and any other components of the resin blend must, of course, be biologically acceptable.

A preferred group of ionomer resins is derived from a copolymer of at least one alpha-olefin and at least one ethylenically unsaturated carboxylic acid and/or anhydride. Suitable alpha-olefins include ethylene, propylene, butene-1, pentene-1, hexene-1, heptene-1, 3-methylbutene, and the like. Suitable carboxylic acids and anhydrides include acrylic acid, methacrylic acid, ethacrylic acid, maleic acid, fumaric acid, maleic anhydride, and the like. The foregoing copolymer advantageously contains from about 0.2 to about 20 mole percent, and preferably from about 0.5 to about 10 mole percent, carboxylic acid groups. Particular examples of such copolymers include ethylene/acrylic acid copolymers, ethylene/methacrylic acid copolymers, ethylene/itaconic acid copolymers, ethylene/methyl hydrogen maleate copolymers, ethylene/maleic acid copolymers, ethylene/acrylic acid/methyl methacrylate copolymers, ethylene/methacrylic acid/ethylacrylate copolymers, ethylene/itaconic acid/methyl methacrylate copolymers, ethylene/methyl hydrogen maleate/ethyl acrylate copolymers, ethylene/methacrylic acid/vinyl acetate copolymers, ethylene/acrylic acid copolymers, ethylene/acrylic acid/vinyl alcohol copolymers, ethylene/acrylic acid/carbon monoxide copolymers, ethylene/propylene/acrylic acid copolymers, ethylene/methacrylic acid/acrylonitrile copolymers, ethylene/fumaric acid/vinyl methyl ether copolymers, ethylene/vinyl chloride/acrylic acid copolymers, ethylene/vinylidene chloride/acrylic acid copolymers, ethylene/vinylidene chloride/acrylic acid copolymers, ethylene/vinyl fluoride/methacrylic acid copolymers, and ethylene/chlorotrifluoroethylene/methacrylic acid copolymers. The copolymers may also, after polymerization but prior to ionic crosslinking, be further modified by various reactions to result in polymer modifications which do not interfere with their subsequent ionic crosslinking. Halogenation of an olefin acid copolymer is an example of such polymer modification.

The preferred ionomer resins are obtained by reacting the foregoing copolymers with a sufficient amount of metal ions as to neutralize at least about 5 percent by weight, and preferably from about 20 to about 100 percent by weight, of the carboxylic acid groups present. Suitable monovalent metal ions include $Na^+$, $K^+$, $Li^+$, $C^+$, $Rb^+$, $Hg^+$ and $Cu^+$. Suitable divalent ions include $Be^{+2}$, $Mg^{+2}$, $Ca^{+2}$, $Sr^{+2}$, $Ba^{+2}$, $Cu^{+2}$, $Cd^{+2}$, $Hg^{+2}$, $Sn^{+2}$, $Pb^{+2}$, $Fe^{+2}$, $Co^{+2}$, $Ni^{+2}$, and $Zn^{+2}$. Suitable trivalent metal ions include $A^{+3}$, $Sc^{+3}$, $Fe^{+3}$ and $Y^{+3}$. The preferred metals suitable for neutralizing the copolymers used herein are the alkali metals, particularly cations such as sodium, lithium and potassium, and alkaline earth metals, in particular, cations such as calcium, magnesium and zinc.

Ionomer resins of the preferred type are disclosed, inter alia, in U.S. Pat. Nos. 3,264,272, 3,322,734 and 3,404,134, the contents of which are incorporated by reference herein. Ionomer resins derived from ethylene/methacrylic acid copolymers, e.g., DuPont's Surlyn ® resins, are particularly preferred. Surlyn ® resins 8020 and 8920 provide especially good results, particularly when combined with a crystalline polypropylene as the nonionic thermoplastic resin component of the blend.

It is, of course, within the scope of the present invention to utilize two or more ionomer resins in the blends from which the suture herein is obtained.

The nonionic thermoplastic resin component of the blend from which the suture of this invention is formed can be selected from amongst any of a large variety of such resins and can be, for example, a polyolefin, polyvinyl ether, poly(phenylene ether), acetal resin, thermoplastic polyester, polycarbonate, cellulose ester, thermoplastic polyamide, polyetheramide, polyesteramide, thermoplastic polyurethane, polyvinylhalide, polyvinylidene halide, halogenated polyolefin, acrylic resin, polystyrene, polyacrylonitrile, polyvinylester, polyimide, polyetherimide, polysulfone, etc. Of the foregoing resins, the polyolefins are preferred, in particular, the homopolymers and copolymers of alpha-olefins of from 2 to 6 carbon atoms, e.g., polyethylenes, polymethylbutenes, polymethylpentenes, polypropylenes, polybutenes, polybutadienes, polyisoprenes, chlorinated polyethylenes, copolymers of ethylene and propylene, copolymers of ethylene and/or propylene containing relatively small amounts, e.g., up to about 10 mole percent, of other copolymerized monomers such as vinyl acetate, acrylic acid, methyl acrylate, ethyl acrylate, methyl methacrylate, etc, e.g., blends of two or more different polyethylenes, polypropylenes, etc., polyethylene-polypropylene blends, polyethylene-polybutene blends, etc.

Of the foregoing preferred polyolefins, crystalline polypropylenes of from about 150,000 to about 500,000 average molecular weight ($\overline{Mw}$) are especially preferred. Highly preferred are the isotactic polypropylene resins possessing a weight average molecular weight ($\overline{Mw}$) of from about 200,000 to about 350,000, a number average molecular weight ($\overline{Mn}$) of from about 50,000 to about 180,000 and a calculated dispersity ($\overline{Mw}/\overline{Mn}$) of from about 2.0 to about 4.0. The isotactic polypropylene resins will advantageously possess a melt flow index in g/10 min of from about 2 to about 6 and preferably from about 3.5 to about 4.5. Isotactic polypropylene resins which can be used herein with generally good results include Resin F040A Blue of Aristech Chemical Corporation (Pittsburgh, Pa.) and Profax 6523 of Himont Incorporated (Wilmington, Del.). These resins possess the following characteristics

|  | Aristech F040A | Profax 6523 |
|---|---|---|
| Weight Average Molecular Weight | 283,000[1] | 305,000[2] |
| Number Average Molecular Weight | 61,000[1] | 80,000[2] |
| Melt Flow Index, g/10 min | 4.5 | 3–5 |
| Isotactic Index | 96 | 94 or above |

[1]Measured upon the dyed resin, as reported by the supplier.
[2]In decalin, as reported in the literature.

The individual components of the blend herein can be melt-mixed or solution-blended. The blend must be compatible, i.e., it must be homogeneous or heterogeneous on a microscopic scale and must not exhibit any obvious inhomogeneity on a macroscopic scale. A blend that is heterogeneous on a macroscopic scale can be rendered compatible by addition thereto of a compatibilizing agent as is well known in the art. For details concerning compatibilizing agents, reference may be made to such sources as the "Encyclopedia of Polymer Science and Engineering", Mark et al., eds, Vol. 3, pp. 771-774 (John Wiley & Sons, Inc. 1985), the contents of which are incorporated by reference herein.

The filament of the present invention is fabricated from a blend of ionomer resin and nonionic thermoplastic resin containing from about 1 to about 99 parts by weight of ionomer resin, preferably from about 2 to about 50 parts by weight of ionomer resin, and most preferably from about 5 to about 20 parts by weight of ionomer resin, the balance of the resin content of the blend being made up of the nonionic thermoplastic resin.

The blend can contain varying amounts of one or more optional ingredients incorporated into the ionomer resin and/or nonionic thermoplastic resin components prior to their being blended or into the blend. Such optional ingredients include biologically acceptable plasticizers, antioxidants, stabilizers, fillers, colorants, bioactive substances such as biocidal agents, antibiotics, growth factors, anti-clotting agents, etc., and the like, in the usual amounts.

A particularly advantageous group of optional ingredients where the resin blend is to be formed into a suture or surgical mesh are those bioactive substances that are capable of being ionically bonded to one or both resin components of the blend, e.g., as disclosed in U.S. Pat. No. 5,006,267, the contents of which are incorporated by reference herein. Bioactive substances having this capability include cationic biocidal agents such as cetyl trimethyl ammonium bromide, alkyltrimethyl ammonium chloride, monoalkyldimethyl benzyl ammonium salts, heteroaromatic ammonium salts, bio-quaternary salts, and the like.

The filament of this invention can be made by wet or melt spinning, methods. A preferred procedure involves melt extruding the blend of ionomer resin and nonionic thermoplastic resin to provide a monofilament, cooling the monofilament, stretching the cooled monofilament to effect orientation of the resin molecules and annealing (relaxing) the oriented monofilament.

In general, the conditions of the individual steps of extruding, stretching and annealing can be substantially the same as those disclosed in U.S. Pat. No. 3,630,205, the contents of which are incorporated by reference herein. Similarly, the process can employ much the same type apparatus as that described in U.S. Pat. No. 3,630,205.

FIG. 1 schematically illustrates the extrusion and stretching operations of the resin blend filament manufacturing operation herein which is particularly well suited for the fabrication of a suture. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of a biologically acceptable and compatible ionomer resin-nonionic resin blend, e.g., the ionomer resin-isotactic polypropylene blend of either of Examples 1 and 2, infra, are introduced to the extruder through drier-hopper 12. Motor driven metering pump 13 delivers extruded resin at a constant rate to spin pack 14 and thereafter through spinneret 15 possessing one or more Orifices of desired diameter to provide a molten filament 16 which then enters quench bath 17, e.g., containing water, where the filament solidifies. The distance filament 16 travels after emerging from spinneret 15 to the point where it enters quench bath 17, i.e., the air gap, can vary and can advantageously be from about 0.5 to about 100 cm and preferably from about 1 to about 20 cm. If desired, a chimney (not shown), or shield, can be provided to isolate monofilament 16 from contact by air currents which might otherwise affect the cooling of the monofilament in some unpredictable manner. In general, barrel zone A of the extruder can be maintained at a temperature of from about 180° to 230° C., zone B at from about 200° to 230° C. and zone C at from about 210 to about 230° C. Additional temperature parameters include: metering pump block 13 at from about 205° to about 230° C., spin pack 14 at from about 205° to about 230° C., spinneret 15 at from about 190° to about 230° C. and quench bath 17 at from about 30° to about 80° C.

Entering quench bath 17, monofilament 16 is passed by driven roller 18 over idler rollers 19 and 20 and thereafter is wrapped around a first godet 21 provided with nip roll 22 to prevent slippage which might otherwise result from the subsequent stretching operation. Monofilament 16 passing from godet 21 is stretched in order to effect its orientation and thereby increase its tensile strength. Thus, in one type of stretching operation, generally suitable for smaller sutures, e.g., sizes 4/0 to 8/0, monofilament 16 is drawn through heating unit 23, which can be an oven chamber or a hot water trough, by means of second godet 24 which rotates at a higher speed than first godet 21 thereby stretching the monofilament from three to eight times its original length. Where heating unit 23 is an oven chamber, its temperature is advantageously maintained at from about 60° to about 180° C. and preferably from about 80° to about 120° C. In the case of larger sutures, e.g., sizes 2 to 3/0, it is preferred that heating unit 23 be a hot water trough or bath which is maintained at a temperature of from about 60° to about 98° C. and preferably from about 80° to about 98° C.

For smaller suture sizes, e.g., sizes 6/0 to 8/0, it is preferred to pass the monofilament through a second heating unit, e.g., maintained at a temperature of from about 60° to about 130° C. and preferably from about 80° to about 110° C., by means of a hot air oven to heat-treat the monofilament prior to the annealing operation. This second heat treatment results in on-line relaxation, or shrinkage, of the monofilament, e.g., for a recovery of from about 80 to about 97 percent, and preferably from about 90 to about 95 percent, of the stretched length of the monofilament. In order to accommodate this on-line shrinkage in the monofilament, the third godet is driven at a speed which is somewhat less than that of the second godet.

In the larger suture sizes, e.g., sizes 5/0 and larger, annealing is accompanied by shrinkage of the suture, e.g., for a recovery of from about 80 to about 97 percent, and preferably from about 85 to about 95 percent, and preferably from about 90 to about 95 percent, of its stretched length.

In carrying out the annealing operation, the desired length of suture can be wound around a creel and the creel placed in a heating cabinet maintained at the desired temperature, e.g., 100° C. to 150° C., as described in U.S. Pat. No. 3,630,205. After a suitable period of residency in the heating cabinet, e.g., about 15 minutes or so, the suture will have undergone shrinkage, e.g., to about 85% of the stretched length for sutures of sizes 2 to 3/0, to about 90% of the stretched length for sutures of sizes 4/0 and 5/0 and essentially no shrinkage in the case of sutures of sizes 6/0 to 8/0. As shown in U.S. Pat. No. 3,630,206, the creel can be rotated within the heating cabinet in order to insure uniform heating of the monofilament or the cabinet can be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then ready to be packaged and sterilized.

Figure 5:
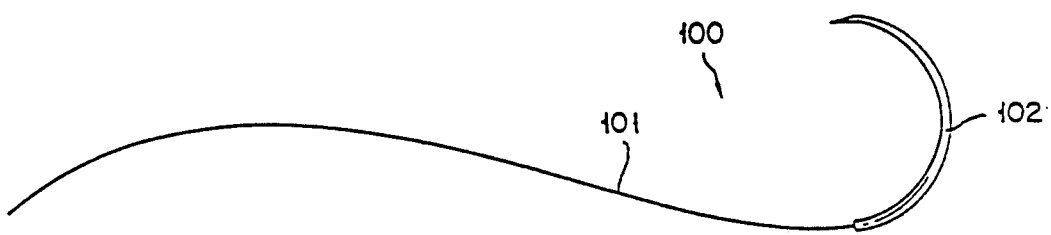

The monofilament, provided it is of suitable diameter, can be used as a suture or it can be used in the construction of a multifilament suture. Multifilament sutures of the present invention may be made by methods well known in the art. Braid constructions such as those disclosed in U.S. Pat. Nos. 5,059,213, 50019,093 and 4,959,069 are suitable for the multifilament sutures of the present invention. The suture can be coated or filled with substances which improve its functional characteristics, e.g., its lubricity, its knot tie down properties, etc. Similarly, the suture can be coated with one or more substances which enhance its usefulness as a wound closure device, e.g., with any of the bioactive substances previously mentioned. FIG. 5 illustrates a combined suture-surgical needle device 100 in which monofilament suture 101 is attached to surgical needle 102. Suturing with combined suture-surgical device 100 is accomplished in accordance with accepted surgical practice, i.e., with repeated passes of needle 102 through approximated tissue at the wound site to ligate the wound followed by tying a knot in the suture and removing the needle.

The following examples are illustrative of the filament of this invention intended for use as a suture and a preferred process for its manufacture.

Table I below sets forth typical conditions for the extruding, stretching and annealing operations used in manufacturing the suture of this invention. The individual resins employed were Surlyn ® 8020 ionomer resin and Aristech F040A isotactic polypropylene.

TABLE I

MONOFILAMENT SUTURE MANUFACTURING CONDITIONS

| Example | Comparative | 1 | 2 |
|---|---|---|---|
| Suture Size | 3/0 | 3/0 | 3/0 |
| Ionomer Resin/Polypropylene Blend (Weight percent) | 0/100 | 5/95 | 10/90 |

| Composition Process Conditions | Extrusion Operation | | |
|---|---|---|---|
| extruder screw, rpm | 15.9 | 15.4 | 14.5 |
| metering pump rpm | 7.35 | 15.2 | 15.2 |
| barrel temp., °C., zone A | 200 | 190 | 210 |
| barrel temp., °C., zone B | 210 | 210 | 210 |
| barrel temp., °C., zone C | 210 | 215 | 220 |
| clamp temp., °C. | 205 | 210 | 220 |
| pump temp., °C. | 205 | 210 | 215 |
| block temp., °C. | 205 | 210 | 215 |
| spinneret, °C. | 205 | 195 | 215 |
| barrel pressure, psi | 2300 | 2600 | 2085 |
| metering pump pressure, psi | 1900 | 2400 | 1796 |
| spinneret pressure, psi | 1250 | 1860 | 1886 |
| metering pump size, cc/rev. | 1.17 | 0.584 | 0.584 |
| diameter of orifices, mm | 0.75 | 0.75 | 0.75 |
| quench bath temp., °C. | 65 | 25 | 34 |

| Process Conditions | Stretching (Orientation) Operation | | |
|---|---|---|---|
| draw bath temp., °C. | 86 | — | — |
| oven temp., °C. | — | 90 | 90 |
| first godet speed, mpm | 7.3 | 7.3 | 7.4 |
| second godet speed, mpm | 48.7 | 48.3 | 48.6 |
| raw ratio | 6.7 | 6.6 | 6.6 |

| Process Conditions | Annealing (Relaxation) Operation | | |
|---|---|---|---|

TABLE I-continued

| oven temp., °C. | 150 | 130 | 130 |
|---|---|---|---|
| time, min | 10 | 15 | 15 |
| shrinkage as % recovery of stretched length | 90 | 85 | 85 |

The physical properties of the sutures and the procedures employed for their measurement are set forth in Table II as follows:

TABLE II

PROCEDURES FOR MEASURING PHYSICAL PROPERTIES OF MONOFILAMENT SUTURES

| Physical Property | Test Procedure |
|---|---|
| knot-pull, strength, kg | U.S.P. XXI, tensile strength, sutures (881) |
| straight-pull strength, kg | ASTM D-2256, Instron Corporation |
| elongation % | ASTM D-2256 |
| tensile strength, kg/mm$^2$ | ASTM D-2256, Instron Corporation Series IX Automated Materials Testing System 1.03A |
| 0–5% and 0–10% strain energies, kg-mm | ASTM D-2256, Instron Corporation Series IX Automated Materials Testing System 1.03A |
| knot security | A 2 cm loop is tied with a surgeon's square knot (1 = 1 = 1 = 1) securing the throws at 20% of the USP XXII knot strength for nonabsorbable sutures (n = 10 loops per group). The loop is placed next to a cloth-wrapped mandrel rotating at .5 rpm. The fixtures are secured to allow contact of the cloth material against the fourth throw or, top throw, of each knot. The cloth wrapping is moistened with 37° C. water prior to the test and is periodically remoistened during the test. Each pass of the cloth across the knot (for a total of 100 passes), the knot is inspected for top throw security. For a knot to be considered secure, the 3 mm ears must not come undone and there must be no relaxation of the knot or loss of the fourth throw. |

Table III below sets forth the physical properties of the foregoing sutures.

TABLE III

| Physical Property | Comparative Example | Example 1 | Example 2 |
|---|---|---|---|
| diameter (mm) | 0.238 | 0.245 | 0.245 |
| knot-pull strength (kg) | 1.43 | 1.55 | 1.55 |
| straight-pull strength (kg) | 1.76 | 1.64 | 1.58 |
| strain energy 0–5% (kg-mm) | 1.10 | 0.79 | 0.72 |
| strain energy 0–10% (kg-mm) | 4.48 | 4.15 | 4.02 |
| elongation (%) | 40.2 | 39.5 | 38.1 |
| tensile strength (kg/mm$^2$) | 39.6 | 34.8 | 33.5 |
| knot security* | 0/10 | 0/10 | 0/10 |

*Number of knot failures out of 10 samples tested to 100 cycles.

Figure 2:
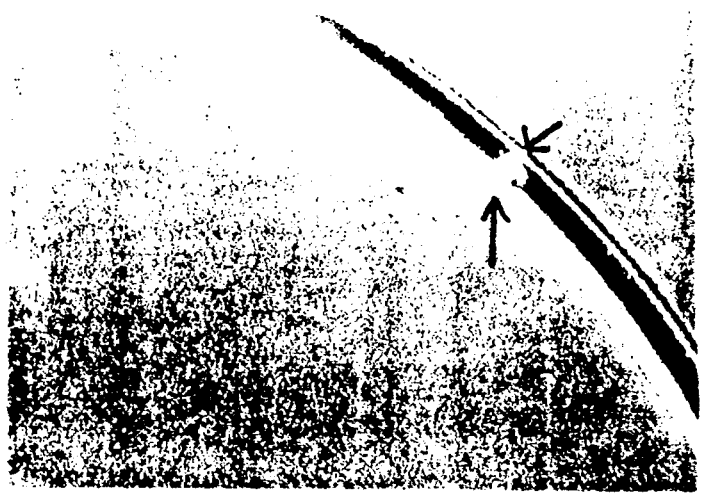
FIG. 2 is a photomicrograph of a linear section of suture fabricated entirely from isotactic polypropylene with arrows pointing to a void.
Figure 3:
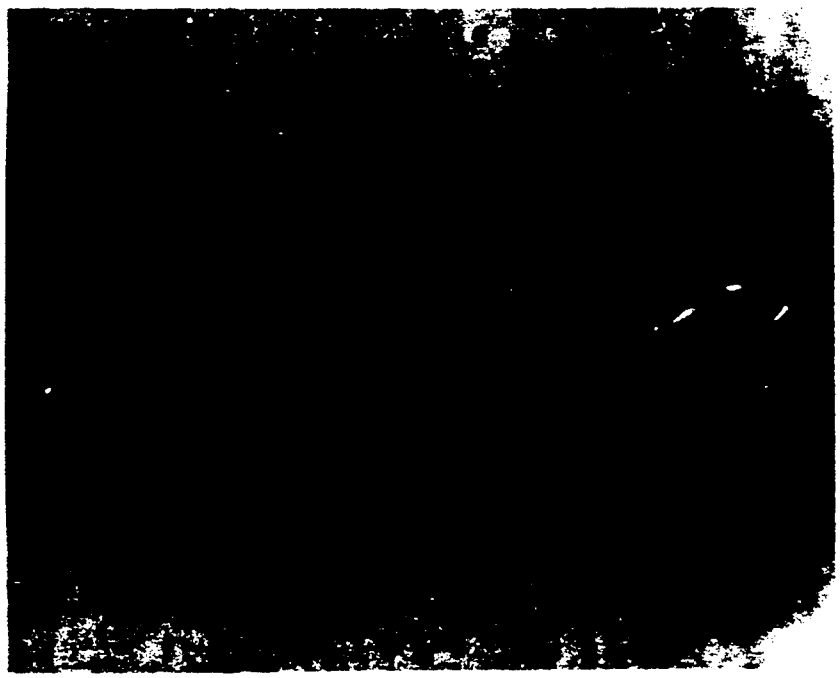
FIG. 3 is a photomicrograph of a cross section of suture fabricated entirely from isotactic polypropylene showing the geometry of the void.
Figure 4:
FIG. 4 is a photomicrograph of an essentially void-free suture fabricated from a blend of ionomer resin and isotactic polypropylene in accordance with this invention; and, FIG. 5 illustrates a combined suture-needle device made with the suture of this invention.

As these data show, the 0–5% and 0–10% strain energies for the sutures of this invention (Examples 1 and 2) were significantly less than those of the suture fabricated entirely from the polypropylene resin (Comparative Example). Furthermore, examination of the three sutures revealed that while there were a significant number of voids in the suture of the comparative example (FIGS. 2 and 3) voids were substantially absent from the sutures of this invention (FIG. 4).

What is claimed is:

1. A medical device comprising a filament fabricated from a biologically acceptable resin blend comprising ionomer resin and nonionic thermoplastic resin.

2. The device of claim 1 wherein the blend contains from about 1 to about 95 parts by weight of ionomer resin based on the total weight of the blend.

3. The device of claim 1 wherein the blend contains from about 2 to about 50 parts by weight of ionomer resin based on the total weight of the blend.

4. The device of claim 1 wherein the blend contains from about 5 to about 20 parts by weight of ionomer resin based on the total weight of the blend.

5. The device of claim 1 wherein the ionomer resin is based on a copolymer of at least one alpha olefin and a member selected from the group consisting of ethylenically unsaturated carboxylic acids and carboxylic acid anhydrides.

6. The device of claim 1 wherein the ionomer resin is based on a copolymer of ethylene and methacrylic acid.

7. The device of claim 1 wherein the nonionic thermoplastic resin is a polyolefin.

8. The device of claim 1 wherein the nonionic thermoplastic resin is a crystalline polypropylene.

9. The device of claim 1 wherein the nonionic thermoplastic resin is an isotactic polypropylene having a melt flow index, in g/10 min, of from about 2 to about 6.

10. The device of claim 1 wherein the blend contains from about 1 to about 40 parts by weight of ionomer resin, the ionomer resin is based on a copolymer of an alpha olefin and an ethylenically unsaturated carboxylic acid and the nonionic thermoplastic resin is an isotactic polypropylene.

11. A suture fabricated from a biologically acceptable resin blend comprising ionomer resin and nonionic thermoplastic resin.

12. The suture of claim 11 which is of monofilament construction.

13. The suture of claim 11 which is of multifilament construction.

14. The suture of claim 11 wherein the blend contains from about 1 to about 99 parts by weight of ionomer resin based on the total weight of the blend.

15. The suture of claim 11 wherein the blend contains from about 2 to about 50 parts by weight of ionomer resin based on the total weight of the blend.

16. The suture of claim 11 wherein the blend contains from about 5 to about 20 parts by weight of ionomer resin based on the total weight of the blend.

17. The suture of claim 11 wherein the ionomer resin is based on a copolymer of at least one alpha olefin at a member selected from the group consisting of ethylenically unsaturated carboxylic acids and carboxylic acid anhydrides.

18. The suture of claim 11 wherein the ionomer resin is based on a copolymer of ethylene and methacrylic 19. The suture of claim 11 wherein the nonionic thermoplastic resin is a polyolefin.

20. The suture of claim 11 wherein the nonionic thermoplastic resin is a crystalline polypropylene.

21. The suture of claim 11 wherein the nonionic thermoplastic resin is an isotactic polypropylene having a melt flow index, in g/10 min, of from about 2 to about 6.

22. The suture of claim 11 wherein the nonionic thermoplastic resin is an isotactic polypropylene having a melt flow index, in g/10 min, of from about 2.5 to about 4.5.

23. The suture of claim 11 wherein the nonionic thermoplastic resin is an isotactic polypropylene possessing a weight average molecular weight of from about 200,000 to about 350,000 and a number average molecular weight of from about 50,000 to about 180,000.

24. The suture of claim 11 wherein the blend contains from about 1 to about 40 parts by weight of ionomer resin, the ionomer resin is based on a copolymer of an alpha olefin and an ethylenically unsaturated carboxylic acid and the nonionic thermoplastic resin is an isotactic polypropylene.

25. The suture of claim 11 containing at least one bioactive substance ionically bonded to the ionomer resin.

26. A surgical mesh fabricated from a biologically acceptable resin blend comprising ionomer resin and nonionic thermoplastic resin.

27. A suture fabricated from a filament obtained by the process comprising melt extruding a biologically acceptable and compatible resin blend comprising ionomer resin and nonionic thermoplastic resin to provide a monofilament, cooling the monofiliment, stretching the cooled monofilament and annealing the stretched monofilament.

28. A suture fabricated from a filament obtained by the process of claim 27 wherein extruding is carried out at from about 180° to about 250° C., stretching is carried out from about 60 to about 180° C. at a stretch ratio of from about 3 to about 8 and annealing is carried out at from about 60 to about 160° C. with recovery to within about 80 to about 97 percent.

29. A suture fabricated from a filament obtained by the process of claim 27 wherein the blend contains from about 1 to about 40 parts by weight of ionomer resin, the ionomer resin is based on copolymer of an alpha olefin and an ethylenically unsaturated carboxylic acid and the nonionic thermoplastic resin is an isotactic polypropylene, extruding is carried out at from about 190 to about 230° C., stretching is carried out from about 80 to about 120° C. at a stretch ratio of from about 5 to about 7 and annealing is carried out at from about 100 to about 150° C. with recovery to within about 85 to about 95 percent.

30. The suture of claim 27 containing at least one bioactive substance ionically bonded to the ionomer resin.

31. A process of closing a wound comprising:
providing a suture fabricated from a biologically acceptable resin blend comprising ionomer resin an nonionic thermoplastic resin; and
suturing said wound closed with said suture.

32. A process as in claim 31 wherein the suture contains at least one bioactive substance ionically bonded to the ionomer resin.

33. A process of hernia repair comprising:
providing a surgical mesh fabricated from a biologically acceptable resin blend comprising ionomer resin and nonionic thermoplastic resin; and
employing said mesh in repairing a hernia.

* * * * *